(12) United States Patent
Bilton et al.

(10) Patent No.: US 10,549,046 B2
(45) Date of Patent: Feb. 4, 2020

(54) DRIVE MECHANISM FOR A DRUG DELIVERY DEVICE

(71) Applicant: Sanofi, Paris (FR)

(72) Inventors: Simon Lewis Bilton, Warwickshire (GB); Robert Veasey, Leamington Spa (GB); Matthew Jones, Warwick (GB); David Aubrey Plumptre, Droitwich Spa (GB); William Marsh, Buckingham (GB); Michael Bainton, Kineton (GB); Daniel David Higgins, Bristol (GB)

(73) Assignee: Sanofi, Paris (FR)

( * ) Notice: Subject to any disclaimer, the term of this patent is extended or adjusted under 35 U.S.C. 154(b) by 574 days.

(21) Appl. No.: 14/914,848

(22) PCT Filed: Sep. 3, 2014

(86) PCT No.: PCT/EP2014/068650
§ 371 (c)(1),
(2) Date: Feb. 26, 2016

(87) PCT Pub. No.: WO2015/032777
PCT Pub. Date: Mar. 12, 2015

(65) Prior Publication Data
US 2016/0220760 A1     Aug. 4, 2016

(30) Foreign Application Priority Data

Sep. 3, 2013    (EP) .................................... 13182755

(51) Int. Cl.
*A61M 5/315*          (2006.01)
(52) U.S. Cl.
CPC .... *A61M 5/31551* (2013.01); *A61M 5/31511* (2013.01); *A61M 5/31568* (2013.01)

(58) Field of Classification Search
CPC .......... A61M 5/31551; A61M 5/31511; A61M 5/31553; A61M 5/31568; A61M 5/31583;
(Continued)

(56) References Cited

U.S. PATENT DOCUMENTS

2008/0234634 A1* 9/2008 Eiland ..................... A61M 5/20
                                                             604/208
2009/0247951 A1   10/2009 Kohlbrenner et al.
(Continued)

FOREIGN PATENT DOCUMENTS

| CN | 102014991 | 4/2011 |
|---|---|---|
| JP | 2010-503433 | 2/2010 |
| WO | WO2008/058665 | 5/2008 |

OTHER PUBLICATIONS

Definition of tactile (Merriam-Webster Jul. 25, 2018).*
(Continued)

*Primary Examiner* — Nathan R Price
*Assistant Examiner* — Dung T Ulsh
(74) *Attorney, Agent, or Firm* — Fish & Richardson P.C.

(57) ABSTRACT

A drive mechanism (1) for use in a drug delivery device (100) is provided. The drive mechanism (1) comprises a housing (10, 11, 12, 14, 15) with a proximal and a distal end and a piston rod (22) which is rotatable with respect to the housing (10, 11, 12, 14, 15). The drive mechanism (1) further comprises a nut member (31) which is selectively rotationally lockable with respect to the housing (10, 11, 12, 14, 15), wherein the drive mechanism (1) is switchable between a setting mode of operation and a dispensing mode of operation. The drive mechanism (1) is configured such that in the setting mode of operation, the nut member (31) and the piston rod (22) are rotatable with respect to the housing (10, 11, 12, 14, 15), and in the dispensing mode of operation, the piston rod (22) is rotatable with respect to the housing (10, 11, 12, 14, 15) and the nut member (31) is
(Continued)

rotationally locked with respect to the housing (10, 11, 12, 14, 15), wherein, when the piston rod (22) rotates, the piston rod (22) moves distally with respect to the nut member (31).

16 Claims, 9 Drawing Sheets

(58) Field of Classification Search
CPC ........ A61M 5/31585; A61M 2205/581; A61M 2205/582
See application file for complete search history.

(56) References Cited

U.S. PATENT DOCUMENTS

| | | | |
|---|---|---|---|
| 2009/0275914 A1 | 11/2009 | Harms et al. | |
| 2010/0312196 A1* | 12/2010 | Hirschel | A61M 5/20 604/207 |
| 2011/0054412 A1 | 3/2011 | Eich et al. | |
| 2011/0056985 A1* | 3/2011 | Bublewitz | B05C 17/00506 222/137 |
| 2012/0089100 A1* | 4/2012 | Veasey | A61M 5/24 604/209 |
| 2012/0197207 A1* | 8/2012 | Stefanski | A61M 5/20 604/189 |
| 2012/0283647 A1* | 11/2012 | Cronenberg | A61M 5/31595 604/207 |
| 2012/0289909 A1* | 11/2012 | Raab | A61M 5/31535 604/211 |
| 2014/0046268 A1* | 2/2014 | Quinn | A61M 5/31575 604/209 |
| 2016/0095981 A1* | 4/2016 | Soerensen | A61M 5/24 604/211 |

OTHER PUBLICATIONS

International Search Report and Written Opinion in International Application No. PCT/EP2014/068650, dated Oct. 11, 2014, 9 pages.
International Preliminary Report of Patentability in International Application No. PCT/EP2014/068650, dated Mar. 8, 2016, 7 pages.
Rote Liste, "50. Hypophysen-, Hypothalamushormone, andere regulatorische Peptide u. ihre Hemmstoffe," Chapter 50, ed. 2008, 20 pages.

* cited by examiner

DRIVE MECHANISM FOR A DRUG DELIVERY DEVICE

CROSS-REFERENCE TO RELATED APPLICATIONS

This application is a U.S. national stage application under 35 USC § 371 of International Application No. PCT/EP2014/068650, filed on Sep. 3, 2014, which claims priority to European Patent Application No. 13182755.2, filed on Sep. 3, 2013, the entire contents of which are incorporated herein by reference.

The present disclosure relates to a drive mechanism for a drug delivery device.

A drug delivery device is, for example, known from WO 2008/058665 A1.

It is an object of the present disclosure to provide an alternative or improved drive mechanism for a drug delivery device and a drug delivery device. With the drive mechanism, the drug delivery device may be implemented particularly cost-effectively and easy to use.

This object is achieved by the subject-matter of the independent claim. Advantageous embodiments and refinements are subject-matter of the dependent claims.

One aspect of the present disclosure relates to a drive mechanism for use in a drug delivery device.

A further aspect of the present disclosure relates to a drug delivery device comprising the drive mechanism.

In an embodiment, the drug delivery device is a pen-type device.

In an embodiment, the drug delivery device is an injector-type device. To this effect, the drug delivery device may comprise a needle or a needle assembly through which a drug may be dispensed from the drug delivery device. Alternatively, the drug delivery device may be a needle-free device. Furthermore, the drug delivery device may be designed for use by persons without formal medical training such as patients including children and adults.

The drug delivery device may further comprise a cartridge containing a drug. The cartridge may further comprise a piston which is movably retained in the cartridge. The drive mechanism may be designed to move the piston distally with respect to the cartridge to dispense a dose of the drug from the cartridge.

In an embodiment, the drive mechanism comprises a housing having a proximal end and a distal end. The housing may be a housing assembly comprising a plurality of housing parts, as for instance a cartridge holder. Preferably, said housing parts are mechanically locked with respect to each other. The housing may expediently house or retain further components of the drive mechanism. The housing of the drive mechanism may also form a housing of the drug delivery device.

In an embodiment, the drive mechanism is switchable between a setting mode of operation and a dispensing mode of operation. Preferably, the drive mechanism is configured such that in the setting mode of operation a dose of the drug can be set and preferably cancelled and in the dispensing mode of operation, the set dose of the drug can be dispensed. The switching may be initiated by the user.

In an embodiment, the drive mechanism comprises a piston rod. The piston rod may be rotatable with respect to the housing, particularly in the setting mode and in the dispensing mode of operation.

In an embodiment, the drive mechanism comprises a nut member. The nut member may mechanically cooperate with the piston rod. For this purpose, the piston rod may be provided with an outer thread and the nut member may be provided with an inner thread. The nut member is preferably threadedly engaged with the piston rod, e.g. via the outer thread of the piston rod and the inner thread of the nut member.

In an embodiment, the nut member is selectively rotationally lockable with respect to the housing.

In an embodiment, the drive mechanism is configured such that in the setting mode of operation, the nut member and/or the piston rod is rotatable with respect to the housing. Preferably, the drive mechanism is configured such that the nut member and the piston rod rotate simultaneously, e.g. such that there is no net rotation between the nut member and the piston rod when, in the setting mode of operation, the nut member and the piston rod rotate with respect to the housing.

In an embodiment, the drive mechanism is configured such that, in the dispensing mode of operation, the piston rod is rotatable with respect to the housing and, particularly, with respect to the nut member. The nut member may be rotationally locked with respect to the housing in the dispensing mode of operation. When the piston rod rotates in the dispensing mode of operation, the piston rod moves distally with respect to the nut member, e.g. due to the mechanical corporation, which may be threaded engagement, between the piston rod and the nut member.

In the setting mode of operation the piston rod does preferably not move axially with respect to the nut member. The piston rod may be arranged to drive the piston retained in the cartridge of the drug delivery device, preferably only in the dispensing mode.

As an advantage of the mentioned embodiments—particularly of the selective rotational locking connection between the nut member and the housing—an implementation of further functional characteristics of the drive mechanism may be facilitated. Additionally, the drug retained in the cartridge may be dispensed from the drug delivery device when the piston rod moves distally with respect to the nut member in the dispensing mode of operation.

In an embodiment, the nut member is axially locked with respect to the housing. As an advantage of this embodiment, it can be achieved that, e.g., in the dispensing mode of operation, when the piston rod moves distally with respect to the nut member, the piston rod is also moved distally with respect to the cartridge which is retained in the cartridge holder. Thereby, a dose of drug may be dispensed from the drug delivery device.

In an embodiment, the nut member is part of a nut assembly further comprising a nut carrier. The nut member may be coupled to the nut carrier. The nut carrier may be rotationally locked to the nut member. It is an advantage of this embodiment that the nut carrier, though being rotationally locked to the nut member, may be axially movable with respect to the nut member. Thus, functions which require an axial movement may be performed by the nut carrier.

In an embodiment, the drive mechanism comprises a selective rotational locking connection which is configured such that in the setting mode of operation, the selective rotational locking connection is released and the nut carrier is rotatable with respect to the housing. In the dispensing mode of operation, the selective rotational locking connection is established, thereby rotationally locking the nut carrier with respect to the housing. A user of the drive mechanism or the drug delivery device may advantageously vary the relative rotation between the nut member and the housing as a parameter during the operation of the drive mechanism by means of the selective rotational locking connection. Particularly, functionality may be provided by which the user may select or set a dose of drug.

In an embodiment, the housing comprises a housing connection element and the nut carrier comprises a carrier connection element, wherein the housing connection element and the carrier connection element are configured to cooperate in order to establish the selective rotational locking connection. Preferably, the housing connection element and the carrier connection element each may comprise ratchet teeth, wherein the ratchet teeth of the housing connection element and the ratchet teeth of the carrier connection element match and the selective rotational locking connection is established when the ratchet teeth of the housing connection element and those of the carrier connection element are engaged.

In an embodiment, the selective rotational locking connection is configured to provide an audible and/or tactile feedback when the nut carrier is rotated with respect to the housing in the setting mode of operation. As an advantage of this embodiment, the user of the drive mechanism may be given feedback or information when the selective rotational locking connection is released and the nut carrier is rotated with respect to the housing in the setting mode of operation. Said feedback may be provided during setting of a dose as well as during cancelling of a dose. The feedback which is provided during setting of a dose may be noticeably different from the one which is provided during cancelling of a dose.

In an embodiment, the drive mechanism comprises a drive member, which mechanically cooperates with the piston rod, wherein the drive member is provided to drive movement of the piston rod in the dispensing mode and, preferably, in the setting mode of operation. The drive member may be rotationally locked with respect to the piston rod.

In an embodiment, the drive mechanism comprises a clutch mechanism operable to releasably rotationally lock the drive member with respect to the nut member. In the setting mode of operation, the drive member is rotationally locked with respect to the nut member, and, in the dispensing mode of operation, the drive member is expediently rotatable with respect to the nut member.

In an embodiment, the drive member comprises a drive clutch feature. The nut carrier may comprise a carrier clutch feature. The drive clutch feature and the carrier clutch feature may be part of the clutch mechanism and configured such that, in a setting mode of operation, the drive clutch feature and the carrier clutch feature are engaged and, in the dispensing mode of operation, the drive clutch feature and the carrier clutch feature are disengaged. When the drive clutch feature and the carrier clutch feature are engaged, a relative rotation of the drive clutch feature and the carrier clutch feature is prevented, preferably in both rotational directions. When the drive clutch feature and the carrier clutch feature are disengaged, a relative rotation of the drive clutch feature and the carrier clutch feature is allowed. Both the drive clutch feature and the carrier clutch feature may comprise splines which mutually match. The clutch mechanism may be configured such that, in the setting mode of operation, the splines of the drive clutch feature and the splines of the carrier clutch feature are engaged and in the dispensing mode of operation, the splines of the drive clutch feature and the splines of the carrier clutch feature are not engaged. In order to switch, e.g. the drive mechanism from the setting mode to the dispensing mode of operation, the drive clutch feature and the carrier clutch feature may be disengaged.

In an embodiment, the drive mechanism comprises a clutch spring which may be part of the clutch mechanism. The clutch spring may be arranged to prevent release of the rotational locking of the nut carrier and the drive member. The clutch spring may be retained between the drive member and the nut carrier, thereby tending to move the drive member and the nut carrier axially away from each other. For switching from the setting mode to the dispensing mode of operation, the clutch spring force may have to be overcome.

In an embodiment, the drive mechanism comprises a trigger member which is operable to switch the drive mechanism from the setting mode of operation to the dispensing mode of operation. The trigger member is preferably configured to disengage or engage the drive clutch feature and the carrier clutch feature upon a respective actuation or release of the trigger member by the user.

The trigger member may be moved relative to the housing for switching from the setting mode to the dispensing mode and, preferably, vice versa. Particularly, the trigger member may be moved axially, preferably distally with respect to the housing in order to switch the drive mechanism from the setting mode to the dispensing mode of operation or vice versa. The trigger member may be moved from a setting position to a dispensing position. In the dispensing position, the trigger member may have to be held by the user against the resilience of a spring, as for instance a clutch spring. The spring may tend to push the trigger member back to the setting position.

In an embodiment, the clutch mechanism is configured such that, when the drive mechanism is in the setting mode of operation and, the trigger member is operated, the drive member is moved distally with respect to the nut member. Thereby, the drive clutch feature and the carrier clutch feature are disengaged and the drive mechanism is switched from the setting mode into the dispensing mode of operation.

The trigger member may be a button. The trigger member may be used to activate the drive mechanism such that a dose of the drug of a previously set size may be dispensed from the drug delivery device.

In an embodiment, the drive mechanism comprises a dial member which is configured to be rotated by the user with respect to the housing in the setting mode of operation to set a dose. The dial member may be rotationally locked to the piston rod. The dose which is set in the setting mode of operation is preferably to be dispensed in the dispensing mode of operation. The size of the dose may be varied by manipulating the dial member.

By the rotational locking of the dial member and the piston rod, the user of the drive mechanism may rotate components of the drive mechanism, as for example the drive member, the piston rod, the nut member, and/or the nut carrier via the dial member when the drive mechanism is in the setting mode of operation.

In an embodiment, the drive mechanism comprises a display member which is rotatable with respect to the housing. The display member may be arranged and configured to display the set dose through a window which is, e.g., provided by the housing. The display member may be rotationally locked with respect to the dial member, but axially movable with respect to the dial member within certain limits.

In an embodiment, the drive mechanism is configured such that, in the setting mode of operation, the nut member and the piston rod are rotatable in a first direction with respect to the housing, when a dose is set. Preferably, the drive mechanism is configured such that the dial member, the drive member, the piston rod, the nut carrier, the nut member and/or further components of the drive mechanism, as for instance the display member, rotate simultaneously, when a dose is set.

In an embodiment the drive mechanism is configured such that in the setting mode of operation the nut member and the piston rod are rotatable in a second direction, opposite to the first direction with respect to the housing, when the set dose is cancelled. Preferably, the drive mechanism is configured such that the dial member, the drive member, the piston rod, the nut carrier, the nut member and/or further components of the drive mechanism, as for instance the display member rotate simultaneously, when the set dose is cancelled.

Preferably, the drive mechanism is configured such that the dial member, the drive member, the piston rod, the display member and/or possibly further components of the drive mechanism, rotate simultaneously, when the set dose is dispensed. Thereby, the nut carrier and the nut member, preferably, do not rotate, as the drive member is free to rotate with respect to the nut carrier and as the nut carrier is selectively rotationally locked with respect to the housing.

In an embodiment, the drive mechanism comprises a drive spring. The drive spring is mechanically coupled to the drive member and the housing. Thereby, the drive spring is arranged and configured such that the drive spring is biased when the dial member is operated to set a dose in the setting mode of operation such that energy is stored in the drive spring. Furthermore, the drive spring may be arranged and configured such that the drive spring is released in the dispensing mode of operation, whereby the stored energy is used to drive movement of the drive member. Preferably, the drive spring is a torsion spring. This embodiment provides the advantage that a force required to dispense a dose of drug is comparably low, as the movement of the piston rod with respect to the housing may be supported or performed by the drive spring. Preferably, the whole dispensing movement may be driven by the energy which is stored in the drive spring during setting of the dose. Thus, a user-exerted force in addition to the force which is required to operate the trigger member is advantageously not required.

As an advantage of the described embodiments, the drive mechanism may be configured such that the force required to actuate or push the trigger member may be independent from the force required to displace the piston rod with respect to the housing or that one required to displace the piston within the cartridge. The distance the trigger member has to be moved or pressed by the user with respect to the housing may thereby be constant and independent from the set dose. These aspects ease an operation of the drug delivery device and additionally provide a safety aspect.

In an embodiment, the drive mechanism comprises a dose nut which mechanically cooperates with the nut carrier, e.g. the dose nut and the nut carrier are threadedly engaged.

Preferably, the nut carrier comprises an outer thread and the dose nut comprises an inner thread, whereby said threads mutually match.

In an embodiment, the dose nut is rotationally locked with respect to the housing.

In an embodiment, the nut carrier and the dose nut are arranged and configured such that in the setting mode of operation, the nut carrier is rotatable with respect to the dose nut such that a rotation of the nut carrier is converted into an axial movement of the dose nut with respect to the nut carrier. As an advantage of this embodiment, the dose nut may move axially with respect to the nut carrier during setting of a dose of drug.

As the nut carrier is not rotated during the dispensing operation, the position of the dose nut on the nut carrier before a setting operation may represent the amount of drug which may still be dispensed, provided that the dose set by said setting operation is actually dispensed.

In an embodiment, the nut carrier and the dose nut are arranged and configured such that the dose nut abuts a stop feature of the nut carrier when the size of the dose set in the setting mode of operation would exceed the content of drug left in the cartridge. The stop feature is preferably a rotational stop feature, thus preventing further rotational movement of the nut carrier with respect to the dose nut and, on account of the threaded engagement, further relative axial movement of the dose nut and the nut carrier. Thereby, advantageously, also the nut carrier may be prevented from being rotated in the setting mode of operation when the size of the dose set in the setting mode of operation would exceed the volume of drug left in the cartridge, as the dose nut abuts the stop feature and the dose nut is rotationally locked with respect to the housing. Thereby, the setting of a greater dose is prevented by the drive mechanism. This also provides a safety task, as the user is given, e.g. a tactile feedback indicating that, e.g. the cartridge is empty.

In an embodiment, the nut carrier comprises a dispense clicker. The dispense clicker may be arranged and configured to interact with the drive clutch feature of the drive member in the dispensing mode of operation, whereby an audible and/or tactile feedback is provided. The dispense clicker may be embodied as arms or cantilever arms which may be configured to be radially deflected.

The described drive mechanism advantageously comprises a low number of interacting parts, whereby the drive mechanism and/or the drug delivery device may be implemented robustly, safely, and cost-efficiently. Furthermore, the drive mechanism and/or the drug delivery device may be easy to operate by the user.

The drug delivery device may be a disposable, single-use drug delivery device for the injection of variable doses of liquid medicament.

A further aspect of the present disclosure relates to the use of the drive mechanism for an operation of the drug delivery device.

In an embodiment, a drive mechanism for use in a drug delivery device comprises a housing having a proximal and a distal end and a piston rod which is rotatable with respect to the housing. The drive mechanism further comprises a nut member which mechanically cooperates with the piston rod and which is selectively rotationally lockable with respect to the housing. Additionally, the drive mechanism is switchable between a setting mode of operation and a dispensing mode of operation. The drive mechanism is configured such that in the setting mode of operation, the nut member and the piston rod are rotatable with respect to the housing, and in the dispensing mode of operation, the piston rod is rotatable with respect to the housing and the nut member is rotationally locked with respect to the housing, wherein, when the piston rod rotates, the piston rod moves distally with respect to the nut member.

As an advantage thereof—particularly of the selective rotational locking connection between the nut member and the housing—an implementation of further functional characteristics of the drive mechanism may be facilitated. Additionally, the drug retained in the cartridge may be dispensed from the drug delivery device when the piston rod moves distally with respect to the nut member in the dispensing mode of operation. As the piston rod rotates in the setting and in the dispensing mode of operation, a reliable coupling, such as a splined interaction, between piston rod and drive member may be provided, which may increase the reliability of the drive mechanism.

Features which are described herein above and below in conjunction with specific aspects or embodiments also apply for other aspects and embodiments. Further features and advantageous embodiments of the subject matter of this disclosure will become apparent from the following description of the exemplary embodiment in conjunction with the figures, in which.

Figure 1:
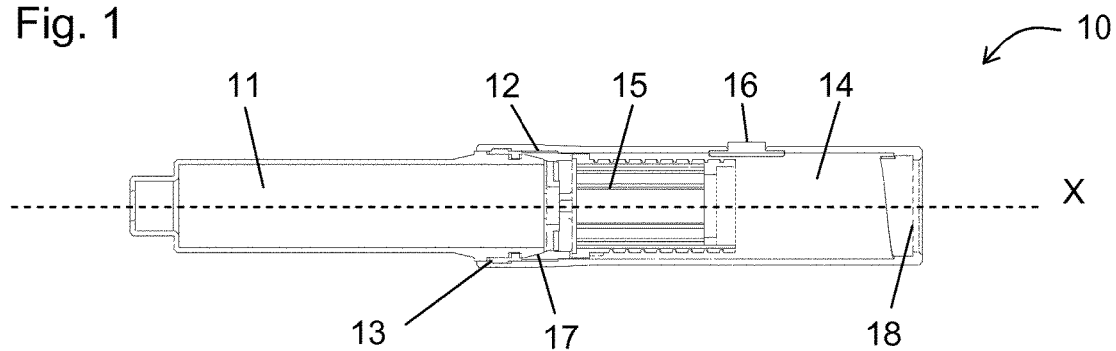
FIG. 1 shows a sectional view of a housing assembly of a drive mechanism.

Like elements, elements of the same kind and identically acting elements may be provided with the same reference numerals in the figures. Additionally, the figures may be not true to scale. Rather, certain features may be depicted in an exaggerated fashion for better illustration of important principles.

Figure 18:
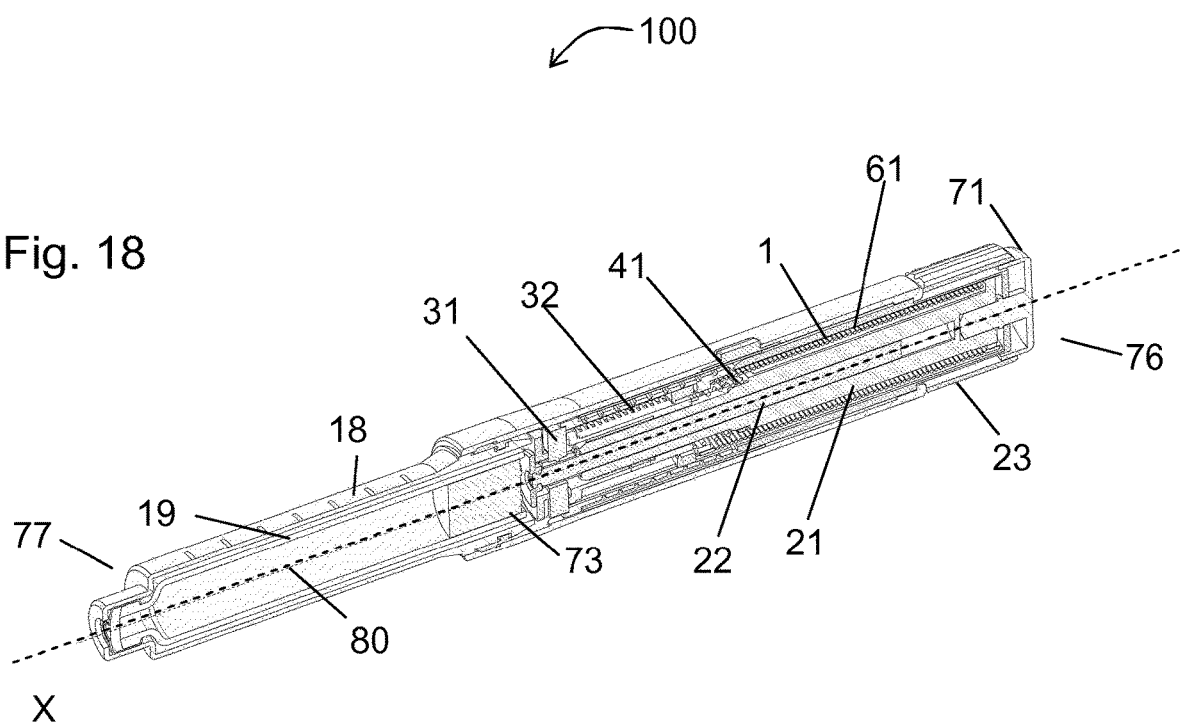
FIG. 18 shows a perspective sectional view of a drug delivery device.

FIG. 18 shows a drug delivery device 100. The drug delivery device 100 comprises a drive mechanism 1 (cf. FIG. 10). The drive mechanism 1 comprises a housing or housing assembly 10 having a proximal end 76 and a distal end 77 (cf. FIG. 1). The housing assembly 10 may also constitute a housing or a housing assembly of the drug delivery device 100. The drive mechanism 1 may be mounted in the housing assembly 10. The drug delivery device 100 comprises a cartridge 19 in which a drug 80 is retained. The drive mechanism 1 and the cartridge 19 may be assembled to form the drug delivery device 100. The drug 80 may be a medicament or a medicinal product. The drug delivery device 100 further comprises a piston 73, which is movably retained in the cartridge. Upon an operation of the drive mechanism 1 which is assembled, the piston 73 may be moved within the cartridge 19, particularly along a longitudinal axis X, such that a dose of drug 80 may be dispensed from the drug delivery device 100. To this effect, the piston 73 may be moved towards the distal end 77 within the cartridge 19. The drug delivery device may be a pen-type device and/or an injector-type device. The drug delivery device may comprise further components which are not explicitly indicated, as, for instance, a needle or a needle assembly or other means to provide fluid communication between the interior of the cartridge and the environment.

Figure 10:
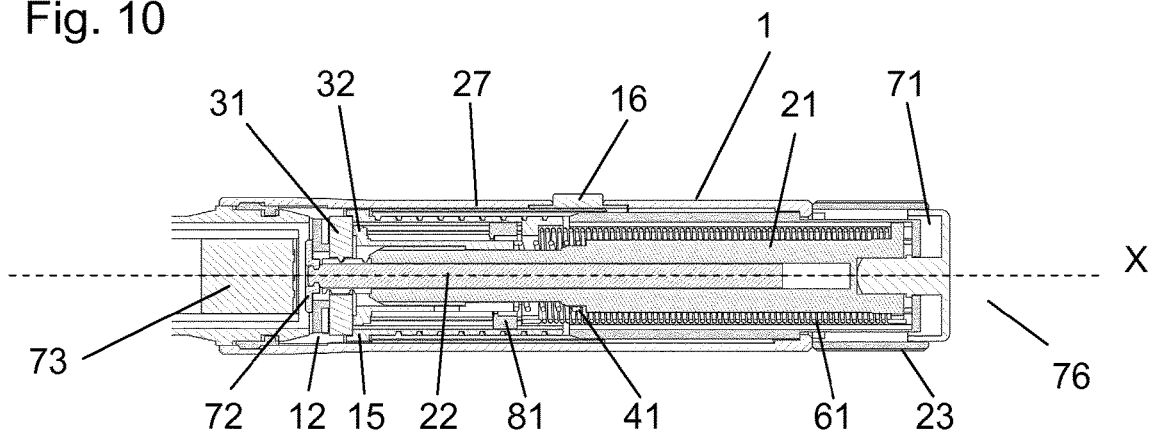
FIG. 10 shows a sectional view of components of the drive mechanism illustrating functions of the drive mechanism.

FIG. 1 shows a housing assembly 10 of the drive mechanism 1 (cf. FIG. 10). The housing assembly 10 further comprises a cartridge holder 11. The cartridge holder 11 houses or retains the cartridge 19. The cartridge 19 may be connected to the housing assembly 10 via a cartridge connection element 17. The housing assembly 10 further comprises an insert 12 which may be affixed to the housing assembly 10 via an insert connection element 13 or formed unitarily therewith.

The housing assembly 10 further comprises an inner housing 15 and a body 14. The insert 12 and the inner housing 15 are retained in and preferably affixed to the body 14. The cartridge holder 11, the insert 12, the body 14 and the inner housing 15 are preferably affixed, particularly mutually locked such that, once assembled, the mentioned components effectively form a single part. The body 14 and the cartridge holder 11 may alternatively be a unitary component. A housing of the drive mechanism may also be formed by the body only. The housing assembly 10 further comprises a window 16 which is preferably transparent such that indicia 59 (cf. FIG. 6), as for instance dose indicia, such as numbers, which are provided in the interior of the housing assembly 10 may be displayed through the window 16. The indicia 59 may indicate the units of drug of the dose currently set to be dispensed by the drug delivery device 100. The window 16 may additionally be convex on either or both of an inner surface and an outer surface of the window 16 such that the indicia 59 may be magnified by means of the window 16. The drive mechanism 1 or additional components of the drug delivery device 100 may be retained in the housing assembly 10 via a retention face 18 of the body 14.

Figure 2A:
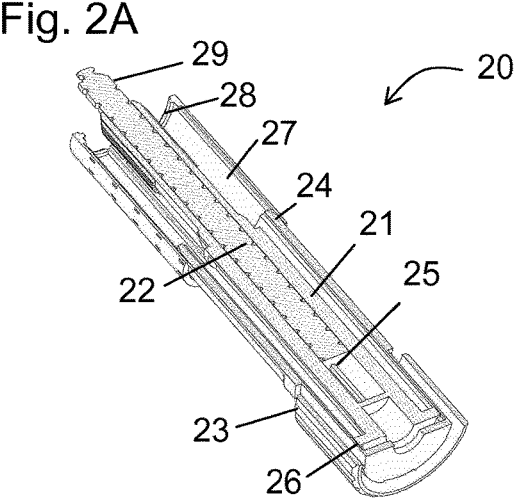
FIG. 2 shows, in FIG. 2A, a sectional perspective view of the drive assembly and, in FIG. 2B, a perspective view of the drive mechanism as a whole.

The drive mechanism 1 further comprises a drive assembly 20. FIG. 2 shows the drive assembly 20 comprising a drive member 21, and a piston rod 22. As shown in the section of FIG. 2A, the drive member 21 is splined to the piston rod 22 via piston rod splines 25 such that the drive member 21 and the piston rod 22 are rotationally locked with respect to each other. The drive assembly 20 further comprises a dial member 23. The dial member 23 is splined to the drive member 21 via drive member splines 26 such that the dial member 23 and the drive member 21 are rotationally locked with respect to each other. The dial member 23 and the drive member 21 may be axially movable with respect to each other. The drive assembly 20 further comprises a display member 27. The display member 27 is splined to the dial member 23 by dial member splines 24 such that the display member 27 and the dial member 23 are rotationally locked with respect to each other. The display member 27 further comprises a display member thread 28. The mentioned components are preferably rotationally locked but axially free to move with respect to each other, preferably within certain limits.

Figure 2B:
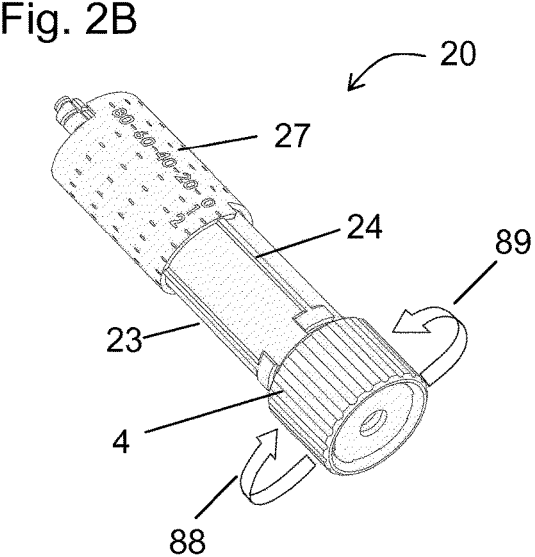

FIG. 2B shows the drive assembly 20 as a whole, wherein, for example, the dial member splines 24 are illustrated. Arrows 88 and 89 indicate a clockwise (88) and counter clockwise rotation (89) of the dial member 23, respectively. Said rotations preferably relate to a rotation with respect to the housing assembly 10. The dial member 23 has an interaction surface 4 which is accessible from the exterior. The interaction surface may be grasped by a user to perform a setting operation for setting a dose of drug.

It is also provisioned that the drive mechanism 1 is configured such that the respective rotation directions are changed with respect to the functionality of the drive mechanism.

Figure 3:
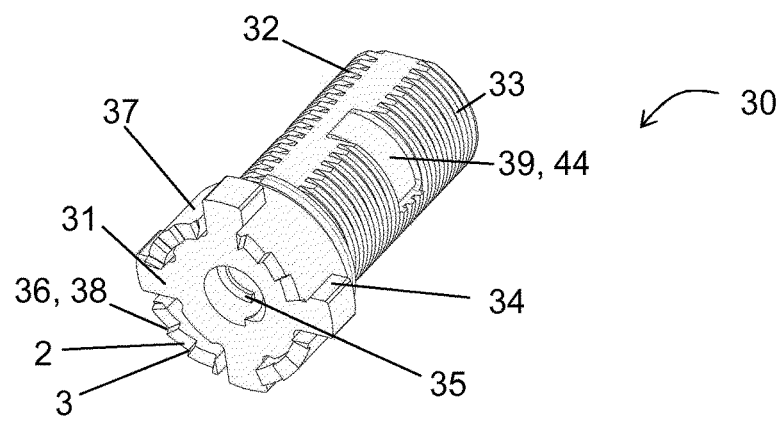
FIG. 3 shows a perspective view of a nut assembly of the drive mechanism.

FIG. 3 shows a nut assembly 30. The nut assembly 30 comprises a nut member 31 and a nut carrier 32. The nut member 31 comprises nut member splines 34 and the nut carrier comprises nut carrier recesses 37 corresponding to the nut member splines 34. The nut member splines 34 extend radially and fit in the nut carrier recesses 37, thereby rotationally locking the nut member 31 and the nut carrier 32. Preferably, when the nut assembly is mounted to the drug delivery device 100 (cf. FIGS. 10 and 18) and/or the drive mechanism 1 is operated, the nut carrier 32 is slightly axially movable with respect to the nut member 31. The nut carrier 32 further comprises a nut carrier thread 33, a dispense clicker 39 (see below) and a carrier connection element 38 comprising nut carrier ratchet teeth 36. The carrier connection element 38 faces in the distal direction and may be arranged at a distal end of the nut carrier 32. The nut member 31 further comprises a nut member thread 35 which matches with the piston rod thread 29 such that the piston rod 22 may be threadedly engaged to the nut member 31.

Figure 4:
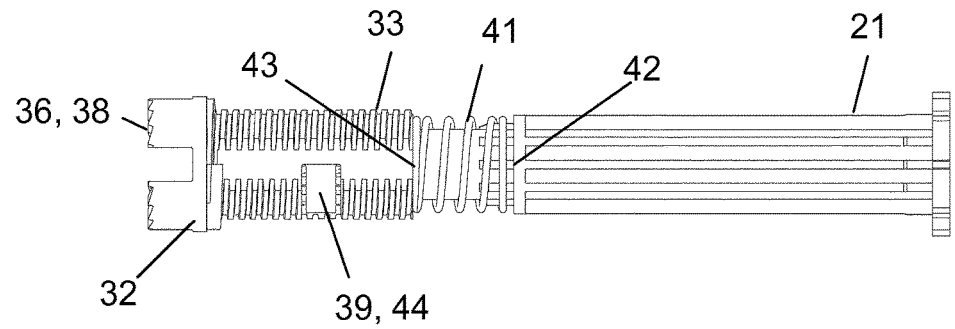
FIG. 4 shows a side view of components of the drive mechanism.

FIG. 4 shows a side view of the nut carrier 32, the drive member 21 and a clutch spring 41. In FIG. 4, a distal end of the drive member is partially inserted in the nut carrier 32 through a proximal opening 50 (cf. FIG. 5B) of the nut carrier 32. The clutch spring 41 is retained between the nut carrier 32 and the drive member 21, particularly between a nut carrier abutment face 43 and a drive member abutment face 42. The clutch spring 41, e.g. a coil spring, may tend to move the nut carrier 32 and the drive member 21 away from each other, when said components are assembled to the drug delivery device 100 and/or when the drive mechanism 1 is operated.

Figure 5A:
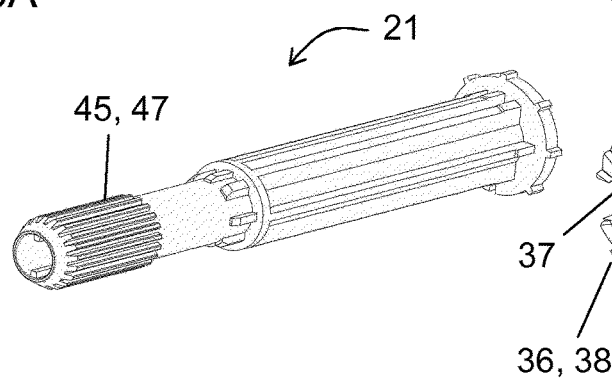
FIG. 5 shows, in FIG. 5A, a perspective view of a drive member of the drive mechanism and, in FIG. 5B, a perspective view of a section of a nut carrier of the drive mechanism.
Figure 5B:
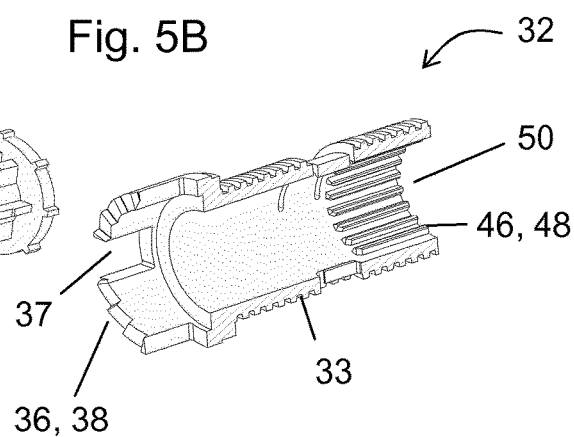

FIG. 5A shows an enlarged perspective view of the drive member 21 comprising a drive clutch feature 45. FIG. 5B shows a perspective sectional view of the nut carrier 32 comprising a carrier clutch feature 46. The drive clutch feature 45 and the carrier clutch feature 46 are part of a clutch mechanism which is operable to releasably rotationally lock the drive member 21 with respect to the nut carrier 32. The drive clutch feature 45 comprises drive clutch splines 47 and the carrier clutch feature 46 comprises carrier clutch splines 48. The drive clutch splines 47 are configured to match with the carrier clutch splines 48, whereby, when said splines are engaged, the nut carrier 32 and the drive member 21 are rotationally locked with respect to each other. The nut carrier 32 and the drive member 21 are furthermore movable, preferably axially movable to disengage the drive clutch splines 47 and the carrier clutch splines 48, whereby the nut member 31 and the drive member 21 are rotationally unlocked and, in this case, are free to rotate relative to each other.

Figure 6:
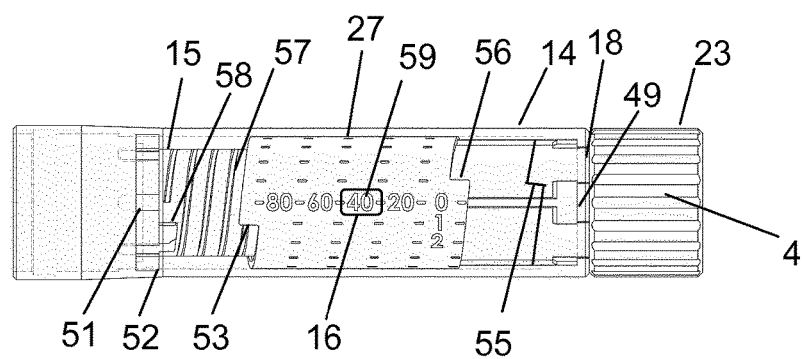
FIG. 6 illustrates a partial side view of the drive mechanism and an interaction between the drive assembly and the housing assembly.

FIG. 6 shows a side view of parts of the drive assembly 20 interacting with the housing assembly 10. The drive assembly 20 is connected to or retained in the housing assembly 10 via a drive assembly connection element 49 and the retention face 18. The body 14 is depicted partially transparent. It is shown that the inner housing 15 comprises an inner housing connection element 51 by which the inner housing 15 may be connected to the body 14. The inner housing 15 may furthermore be retained in the body 14 via a collar 52. The inner housing 15 further comprises an inner housing thread 57. It is further shown in FIG. 6 that the display member 27 comprises a display member end stop face 53 and a display member maximum stop face 56. The housing assembly 10 comprises a body stop 55. During dispensing or setting of a dose of a drug, the number of units is set for a dose to be delivered and visible through the window 16 via the indicia 59 provided on the display member 27. In the embodiment shown in FIG. 6, a number of 40 units is set and visible though the window 16. The drive assembly 20 is rotatable within the housing assembly 10. The extent of this rotation is limited by the interaction of the display member 27 with the body 14 and the inner housing 15. The display member 27 is threadedly engaged to the housing assembly 10 via the inner housing thread 57. When the dial member 23 is rotated clockwise (cf. arrow 88 in FIG. 2A), the display member 21 rotates with it, as the dial member 23 and the display member 21 are rotationally locked and the display member 27 moves along an inner housing thread 57 in the proximal direction, towards the body stop 55. This movement is delimited by the maximum settable dose or the maximum number of units the user may set or select by the drive mechanism 1. When a dose corresponding to the maximum number of units is set by the drive mechanism 1, the display member maximum stop face 56 abuts the body stop 55. The inner housing comprises an inner housing stop 58. When the dial member 23 is rotated counter clockwise, the display member 27 moves along the inner housing thread 57 in the distal direction, towards the inner housing stop 58. When the set dose is zero or the last dose has been dispensed from the drug delivery device 100, the display member end stop face 53 abuts the inner housing stop 58.

The indicia 59 are arranged on the display member 27 in a helical fashion, expediently with the same pitch as the inner housing thread 57. This provides the advantage that either during setting or dispensing of a dose, the number of units visible through the window 16 matches with the units actually set or dispensed. To this effect, the display member 27 indicates zero units through the window 16 when the set dose is zero.

Figure 7:
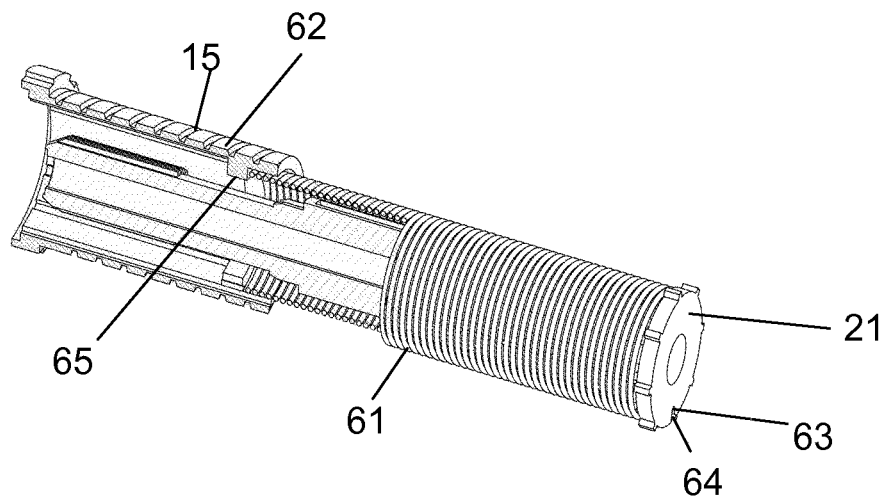
FIG. 7 shows a perspective view of components of the drive mechanism which are partly shown in section.

The drive mechanism 1 further comprises a drive spring 61. FIG. 7 shows in a partial sectional view the inner housing 15, the drive member 21 and the drive spring 61. The drive spring 61 is a torsion spring with multiple coils or windings. The windings are wound such that frictional losses between the coils are reduced, when the drive mechanism is operated. The spring 61 comprises a distal termination 62 and a proximal termination 63. The drive member 21 comprises a drive member recess 64 which is configured to retain the proximal termination 63 of the drive spring 61. The inner housing 15 comprises an inner housing recess 65 which is configured to retain the distal termination 62 of the drive spring 61. The terminations 62 and 63 of the drive spring 61 are aligned parallel to the longitudinal axis X of the drive mechanism 1 such that a relative rotation of the drive member 21 and the inner housing 15 biases the drive spring 61.

Figure 8:
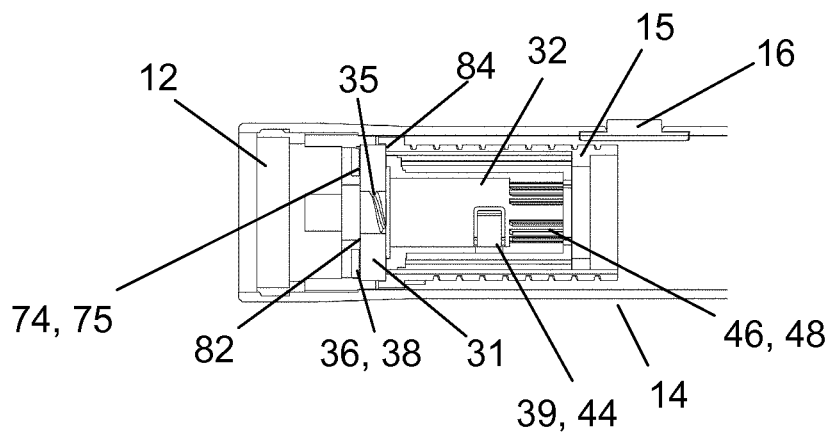
FIG. 8 shows a partial sectional view of components of the drive mechanism illustrating an interaction of the nut assembly and the housing assembly.

FIG. 8 illustrates interactions between the nut assembly 30 and the housing assembly 10. The insert 12 comprises a housing connection element 75 further comprising insert ratchet teeth 74. The nut carrier ratchet teeth 36 of the carrier connection element 38 are engaged here with the ratchet teeth 74. The ratchet teeth 36 and the ratchet teeth 74 are configured to match, thereby forming a selective rotational locking connection. The ratchet teeth 36 and the ratchet teeth 74 extend axially along the longitudinal axis X. The ratchet teeth 36 and 74 are spaced such that each tooth corresponds to a rotation or relative rotation which is required to set a single unit which represents the minimum settable dose. Preferably, the ratchet teeth 36 and 74 each have a triangular section or shape, wherein each of the ratchet teeth 36 and 74 is ramped in both directions, i.e. the clockwise (cf. arrow 88 in FIG. 2A) and the counter clockwise direction (cf. arrow 89 in FIG. 2A). Preferably, the ramps or faces of the ratchet teeth 36 and 74 are inclined with respect to the longitudinal axis X of the drive mechanism 1. This provides the advantage that, after a dose has been set by the user, e.g. by rotating the dial member 23 in a clockwise direction with respect to the housing assembly 10, said dose may be cancelled, e.g. by rotating the dial member 23 in the counter clockwise direction with respect to the housing assembly 10. Particularly, the ramps (cf. 2 in FIG. 3) of the ratchet teeth 36 and 74 corresponding to the clockwise rotation are inclined more with respect to the longitudinal axis X than the ramps (cf. 3 in FIG. 3) of the ratchet teeth 36 and 74 corresponding to the counter clockwise rotation. Preferably, the torque required to cancel a dose of one or more units thereof is determined by the difference of the torque required to overcome the selective rotational locking connection during cancelling of a dose and the torque provided by the drive spring 61. The torque required to overcome the selective rotational locking connection during cancelling of a dose is determined by the ramp angle of the ratchet teeth corresponding to the counter clockwise rotation, the torque provided by the drive spring 61 and the coefficient of static friction between the ratchet teeth 36 and 74.

The nut carrier 32 is axially movable within a small distance range between the nut member 31 and the inner housing 15, wherein the disengagement or release of the ratchet teeth 36 and 74 may require the nut carrier 32 to be axially moved by a distance smaller or equal to the mentioned range. During the disengagement of the nut carrier ratchet teeth 36 and the insert ratchet teeth 74, said components may have to be overwound, whereby an audible and/or tactile feedback is provided to the user during setting of a dose. The piston rod 22 is not shown in FIG. 8. The nut member 31 abuts the insert 12 at a distal nut member abutment face 82. At a proximal end of the nut member 31, the nut member 31 abuts the inner housing 15 at a proximal nut member abutment face 84.

Figure 9:
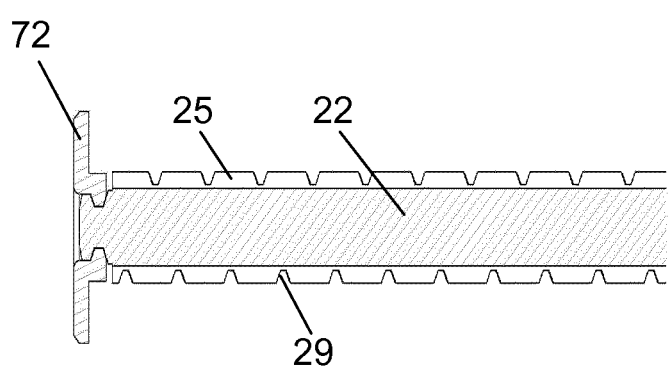
FIG. 9 shows a sectional view of a bearing and partly a piston rod.

FIG. 9 shows a side view of a bearing 72 and a section of the piston rod 22. The FIG. 9 illustrates the piston rod splines 25 by which the drive member 21 is rotationally locked to the piston rod 22. The piston rod thread 29 is shown by which the piston rod 22 is threadedly engaged to the nut member 31. The bearing 72 and the piston rod 22 are configured such that the piston rod 22 is rotatable with respect to the bearing 72. The bearing 72 is furthermore axially locked to the piston rod 22. The contact diameter of the connection of the bearing 72 and the piston rod 22 is expediently small in order to minimize frictional losses upon relative rotation of the bearing 72 and the piston rod 22.

FIG. 10 depicts a section of the drive mechanism 1 as well as further components and illustrates the function of the drive mechanism 1. At least partly, also the housing assembly 10, the drive assembly 20 and the nut assembly 30 are shown, wherein said components are at least partly assembled. The drive mechanism 1 further comprises a dose nut 81 (cf. FIG. 14). The drive mechanism 1 further comprises a trigger member 71. The trigger member 71 is arranged at the proximal end 76 of the drive mechanism 1. The trigger member 71 may be pushed against the resilience of the clutch spring 41 in the distal direction, i.e. to the left in FIG. 10, for initiating delivering a set dose. In FIG. 10, the clutch spring 41 tends to move the drive member 21 and the nut carrier 32 axially away from each other, whereby the ratchet teeth 36 are urged to engage the ratchet teeth 74 in order to establish the selective rotational locking connection. When the ratchet teeth 36 and 74 are disengaged, e.g., upon a rotation of the dial member 23 with respect to the housing assembly 10, the clutch spring 41 is biased. Thereby, the ratchet teeth 36 and 74 are disengaged, whereby a resilience of the clutch spring 41 has to be overcome which corresponds to the range or the axial distance, the nut carrier 32 has to be moved, as mentioned above.

Figure 11A:
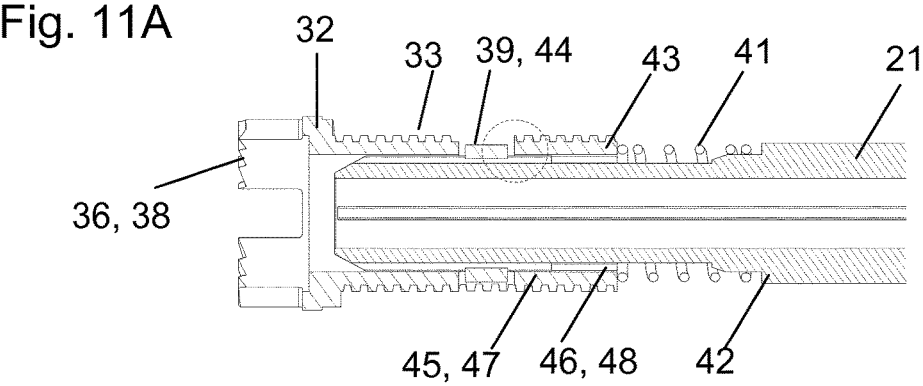
FIG. 11 shows, in FIG. 11A, a sectional view of selected components of the clutch mechanism and, in FIG. 11B, a sectional view of components of the drive mechanism. The drive mechanism is shown here in a setting mode of operation.
Figure 11B:
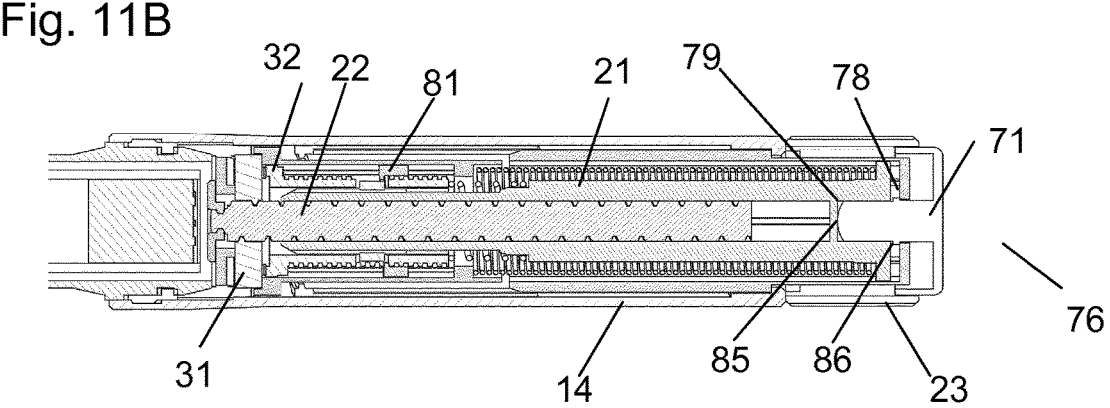
Figure 12A:
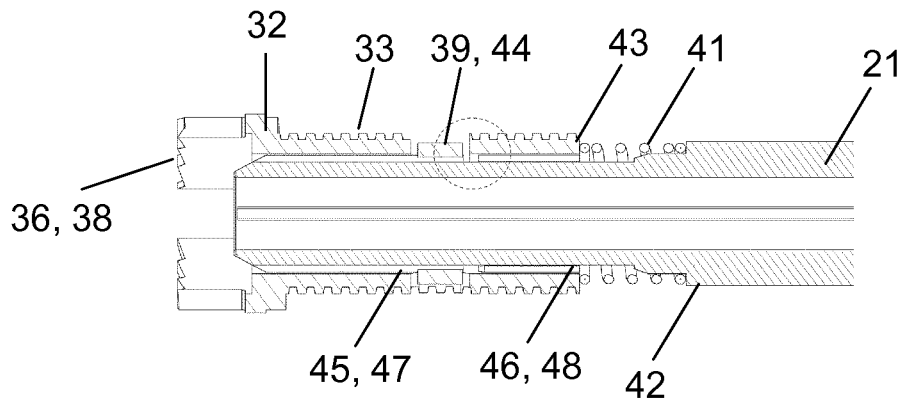
FIG. 12 shows, in FIG. 12A, a sectional view of selected components of the clutch mechanism and, in FIG. 12B, a sectional view of components of the drive mechanism. The drive mechanism is shown here in a dispensing mode of operation.
Figure 12B:
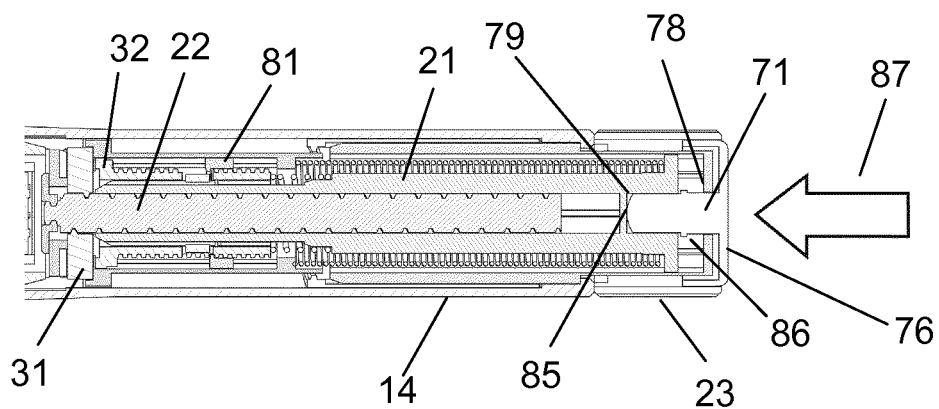

FIGS. 11A and B as well as 12A and B illustrate a function of a clutch mechanism of the drive mechanism 1. The clutch mechanism is operable to releasably rotationally lock the drive member 21 with respect to the nut member 32. In FIGS. 11A and 11B, the drive mechanism 1 is depicted in a setting mode of operation, wherein the clutch mechanism is engaged and a relative rotation of the drive member 21 and the nut carrier 32 is prevented. In FIGS. 12A and 12B the drive mechanism 1 is depicted in a dispensing mode of operation, wherein the clutch mechanism is disengaged and a relative rotation of the drive member 21 and the nut carrier 32 is allowed. In the dispensing mode of operation, the selective rotational locking connection is established.

FIG. 11A shows the drive member 21, the nut carrier 32 and the clutch spring 41. The drive clutch splines 47 and the carrier clutch splines 48 are at least sectionally engaged such that the drive member 21 is rotationally locked with respect to the nut carrier 32 (cf. dashed circle).

FIG. 11B shows the situation, wherein additional components of the drive mechanism 1 are depicted. The drive assembly 20 is free to rotate with respect to the trigger member 71. In FIG. 11B, it is shown that a trigger member face 85 of the trigger member 71 abuts a proximal face 79 of the drive member 21. The trigger member 71 further comprises a protrusion 86 which abuts a distal face 78 of dial member 23 such that the trigger member 71 is held or retained at the proximal end 76 of the drive mechanism 1. A contact face at which the trigger member 71 and the drive member 21 abut is preferably small in order to reduce frictional losses upon a relative rotation of the trigger member 71 and the drive member 23. In the depicted situation, the clutch spring 41 exerts a force in proximal direction on the drive member 21 which in turn effects on the trigger member 71 (via the proximal face 79 and the distal trigger member face 85). Furthermore, said force urges the trigger member 71 in the proximal direction against the dial member 23 such that the distal face 78 abuts the protrusion 86.

FIG. 12A shows a situation, wherein the drive clutch splines 47 and the carrier clutch splines 48 are disengaged such that the drive member 21 is no longer rotationally locked with respect to the nut carrier 32 (cf. dashed circle) but rotatable relative thereto. In contrast to FIG. 11A, the drive member 32 has been switched from the setting mode of operation to the dispensing mode of operation in that the drive member 32 has been moved axially towards the nut carrier 32. Said switch may be carried out by the user by pressing the trigger member 71 distally, as indicated by arrow 87 in FIG. 12B. As a consequence, the drive spring 61 drives rotation of the drive member 21 with respect to the housing assembly 10.

In FIG. 12A, it is shown that the drive clutch splines 47 of the drive clutch feature 45 are still engaged to a dispense clicker 39 of the nut carrier 32. The dispense clicker 39 may comprise clicker arms 44 which are configured to provide an audible and tactile feedback during dispensing of a dose when the drive clutch splines 47 pass the clicker arms 44 upon counter clockwise rotation of the drive member 21 with respect to the nut carrier 32. The drive clutch splines 47 are furthermore configured such that the distance between them corresponds to the rotation required to set or dispense a single unit of drug. Thereby, a user-friendly measure is provided, informing the user audibly and tactile of the number of units dispensed during a dispense operation. Furthermore, the safety of the drug delivery device is increased, as the dispense clicker 39 prevents backwinding of the drive member 21 and the piston rod 22, e.g. when a dispensing operation is interrupted.

Figure 13:
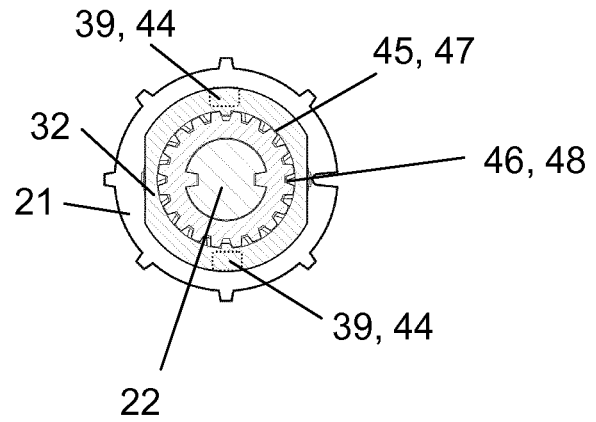
FIG. 13 shows a longitudinal sectional view of selected components of the drive mechanism.

FIG. 13 shows a cross-section through the drive mechanism 1 illustrating the drive member 21, the piston rod 22 and the nut carrier 32 only. The clicker arms 44 are embodied as cantilevers or arms provided by the nut carrier 32. The clicker arms 44 interface radially with the drive clutch splines 47 of the drive clutch feature 45. When the drive member 21 is rotated counter clockwise during dispensing of a dose with respect to the nut carrier 32, the clicker arms 44 deflect radially to allow the drive clutch splines 47 to pass underneath the clicker arms 44. The relaxation of the clicker arms 44 once a drive clutch spline 47 has passed, results in an audible and tactile feedback which occurs for each unit which is dispensed by the drive mechanism 1.

Figure 14:
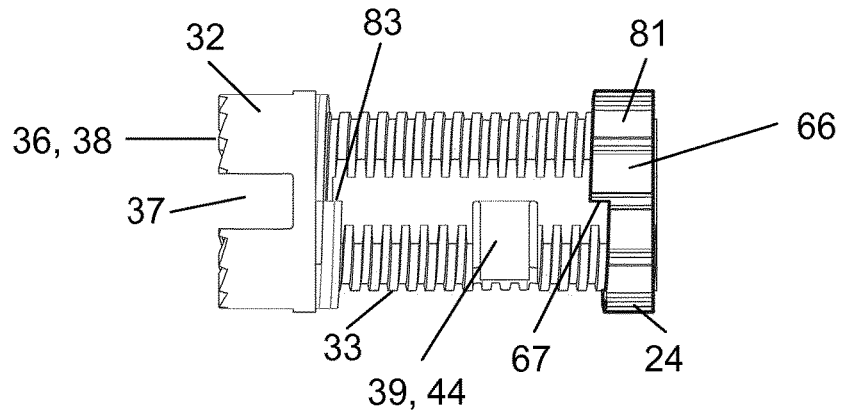
FIG. 14 shows a side view of a nut carrier and a dose nut of the drive mechanism.

FIG. 14 shows a side view of the nut carrier 32 and the dose nut 81. The dose nut 81 is rotationally locked with respect to the housing assembly 10 but axially movable with respect thereto. The dose nut 81 limits the total number of units of drug 80 that can be set by the drive mechanism 1 and subsequently dispensed from the drug delivery device 100. The dose nut 81 is rotationally locked to the inner housing 15 by dose nut splines 66. The dose nut 81 is furthermore threadedly engaged to the nut carrier 32 via the nut carrier thread 33. A rotation of the nut carrier 32, as will occur during the setting of a dose, will cause the dose nut 81 to rotate towards a nut carrier stop face 83 of the nut carrier 32. Once a dose has been set, this dose may be cancelled or reduced by rotation of the dial member 23 in the counter clockwise direction with respect to the housing assembly 10, as mentioned above. Upon reaching the total allowable number of settable units, a dose nut stop feature 67 will abut the nut carrier stop face 83. Thereby, the dose nut 81 will prevent any additional doses from being set, but will allow any set dose to be dispensed, cancelled or reduced.

Figure 15A:
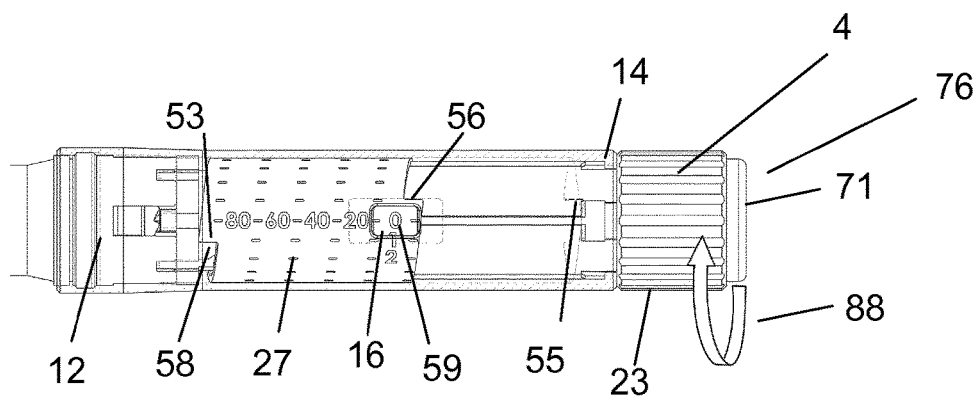
FIG. 15 illustrates, in FIG. 15A, a side view of components of the drive mechanism and, in FIG. 15B, a sectional view of components of the drive mechanism. The drive mechanism is shown in a situation, wherein no dose is set.
Figure 15B:
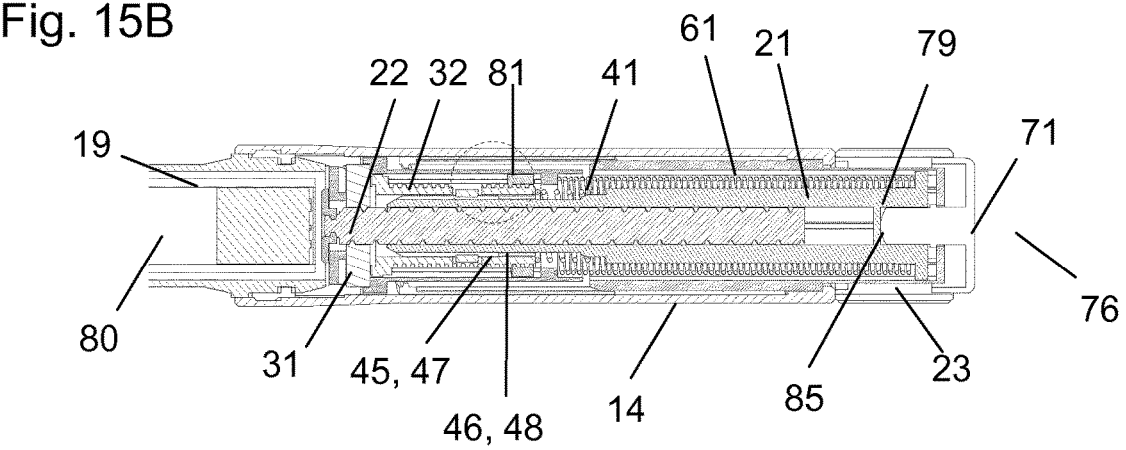

FIGS. 15A and B show the drive mechanism 1 in a situation before a dose is set. FIG. 15A shows a side view of the drive mechanism 1, wherein the body 14 is depicted partially transparent. In FIG. 15B a cross-section of the drive mechanism 1 is shown. The number "0" indicating the number of units on the display member 27 is visible through the window 16. In this situation, the drive spring 61 is already biased such that it exerts a counter clockwise torque on the drive member 21. The drive member 21 is prevented from being rotated counter clockwise by the display member end stop face 53 abutting the inner housing stop 58. In FIG. 15B, it is shown that the clutch mechanism between the drive member 21 and the nut carrier 32 is engaged (cf. dashed circle).

Figure 16A:
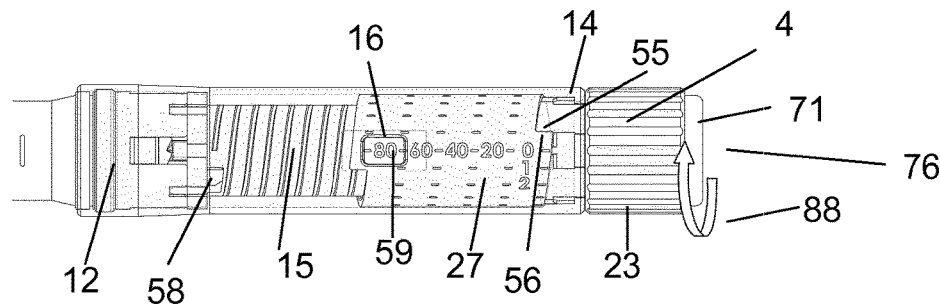
FIG. 16 illustrates the function of setting a dose with the drive mechanism, wherein, in FIG. 16A, a side view of components of the drive mechanism and, in FIG. 16B, a sectional view of components of the drive mechanism are shown.
Figure 16B:
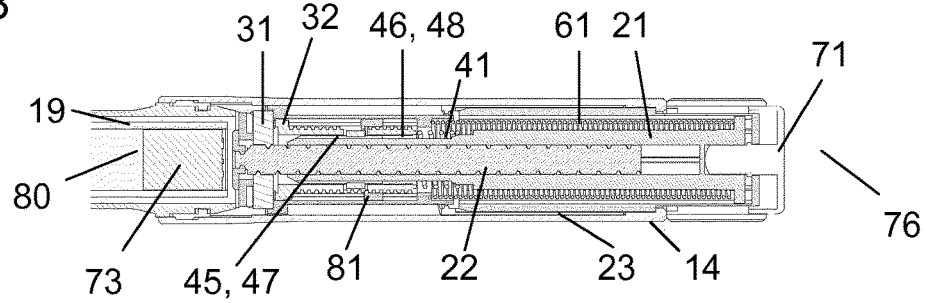

FIGS. 16A and B illustrate the setting of a dose with the drive mechanism 1. The Figures show representations analogue to the ones of the FIGS. 15A and 15B. During setting of a dose, the drive mechanism 1 is in the setting mode of operation and the user has to rotate the dial member in a clockwise direction (cf. arrow 88 in FIG. 2A) with respect to the housing assembly 10, whereby the drive spring 61 is biased. In FIG. 16A, the maximum number of units is set and the display member 27 is shown in its proximal end position such that the display member maximum stop face 56 abuts the body stop 55. The maximum number of units on the display member 27 is visible through the window 16. For setting of a dose, the user has to rotate the dial member 23 clockwise with respect to the housing assembly 10, whereby the ratchet teeth 36 and 74 are disengaged. Thereby, the drive member 21, the display member 27, the nut carrier 32, the nut member 31 and the piston rod 22 rotate along with the dial sleeve 23, whereupon the drive spring 61 is biased such that energy is stored therein. Additionally, the dose nut 81 travels axially towards the nut carrier stop face 83. This is indicated by the arrow in FIG. 16B which directs to the left, i.e. in the distal direction. Preferably, said components or at least the nut member 31 and the piston rod 22 rotate simultaneously such that there is no net rotation between said components or at least the nut member 31 and the piston rod 22, respectively, when—in the setting mode of operation—the nut member and the piston rod rotate with respect to the housing. The rotation of the dial member 23 during dose setting, whereby the number of set units is increased, can be carried out until either the display member maximum stop face 56 abuts the body stop 55 (cf. FIG. 15A) or the dose nut stop feature 67 abuts the nut carrier stop face 83 (cf. FIG. 14). When the dial member 23 is released by the user, the set dose is maintained because the torque required to disengage the ratchet teeth 36 and 74 is greater than the torque of the drive spring 61, even in a situation wherein a maximum number of units is set. At the same time, the torque required to disengage the ratchet teeth 36 and 74 is expediently small enough, so as to enable a user to overcome said torque during setting or cancelling of a dose. Thereby, the inclinations of the ramps 2 and 3 of each of the ratchet teeth 36 and 74 determine the torque required to disengage the ratchet teeth 36 and 74.

Once a dose is set by the user via the interaction surface 4, the dose may be cancelled or a smaller one, may be chosen, i.e. the number of units may be decreased. To cancel a dose, the setting operation is reversed such that the dial member 23 is rotated in the counter clockwise direction by the user, whereby the ratchet teeth 36 and 74 are disengaged. Thereby, the drive member 21, the display member 27, the nut carrier 32, the nut member 21 and the piston rod 22 will rotate together with the dial member 23 in the counter clockwise direction. Thereupon, the torsion or biasing of the drive spring 61 is released. The display member 27 is rotated towards the inner housing stop 58 so that the number of units displayed to the user through the window 16 decreases. The dose nut 81 will thereby be rotated away from the nut carrier stop face 83. The dial member 23 can be rotated in a counter clockwise direction until the display member end stop face 53 abuts the inner housing stop 58. The engagement of the ratchet teeth 36 and 74 will compensate the torque the drive spring 61 exerts on the drive member 21, thus maintaining the selected dose when the user releases the dial sleeve 23.

Figure 17A:
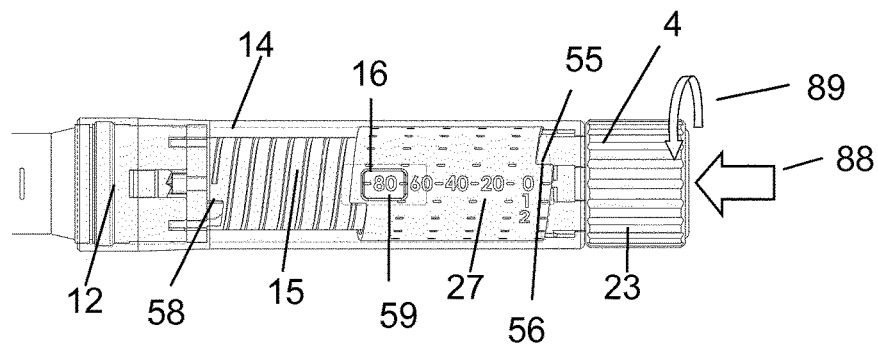
FIG. 17 illustrates the function of dispensing a dose with the drive mechanism, wherein, in FIGS. 17A and 17C a side view of components of the drive mechanism and, in FIGS. 17B and 17D, a sectional view of components of the drive mechanism are shown.
Figure 17B:
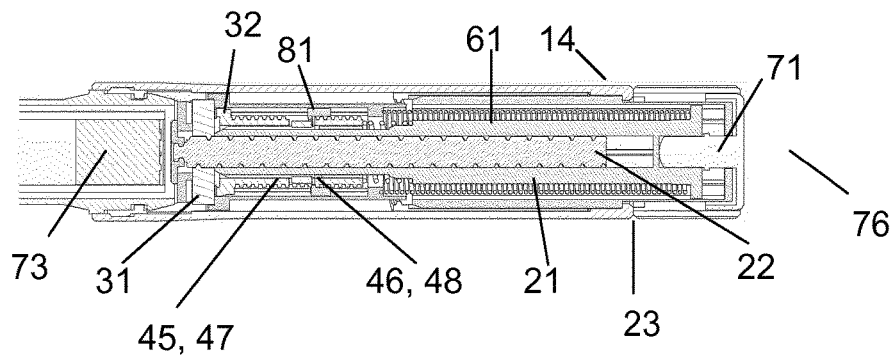
Figure 17C:
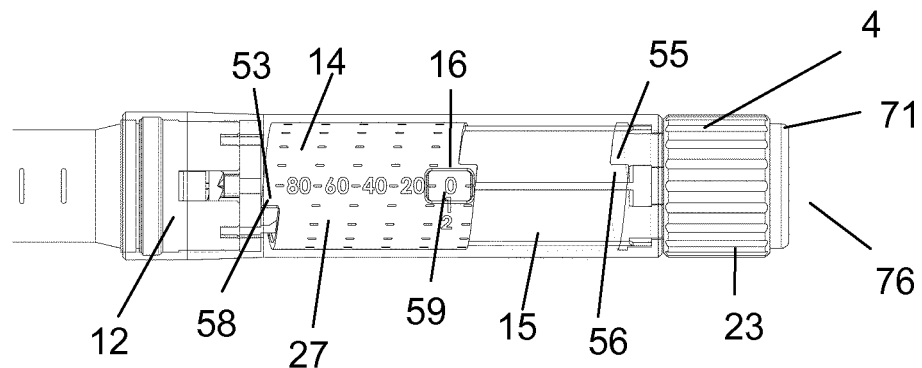
Figure 17D:
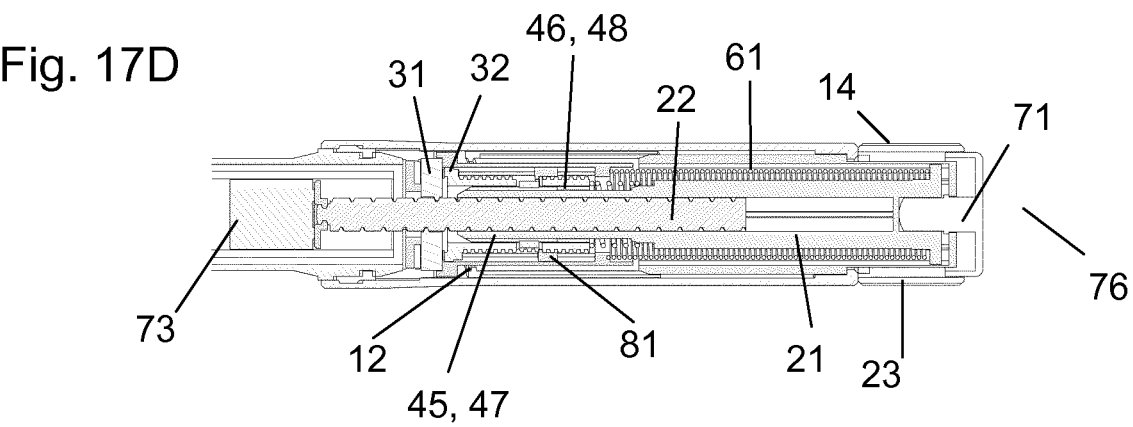

FIGS. 17A to D illustrate the dispensing of a dose from the drug delivery device 100 by the drive mechanism 1. The FIGS. 17A and 17C show representations analogue to the one of the FIG. 15A and the FIGS. 17B and 17D show representations analogue to the one of the FIG. 15B. After a dose has been set, the trigger member 71 may be depressed by the user, in order to initiate the dispensing operation to dispense the previously set dose of drug 80 (cf. arrow 87 in FIG. 12B).

Consequently, the drive mechanism 1 is switched from the setting mode to the dispensing mode of operation, as the trigger member 71 is moved axially from a setting position to a dispensing position. An axial force is applied in the distal direction and the trigger member 71 acts on the drive member 21 via the distal trigger member face 85 and the proximal face 79 of the drive member 21. Thereby, the clutch mechanism between the drive member 21 and the nut carrier 32 is disengaged such that the drive member 21 is rotatable with respect to the nut carrier 32. The nut carrier 32 remains rotationally locked with respect to the housing assembly 10 via the engagement of the ratchet teeth 36 and 74. Consequently, the drive spring 61 is released and the drive member 21 is rotated in the counter clockwise direction (cf. arrow 89 in FIG. 2A). This rotation is driven by the spring force of the drive spring 61 or, as the case may be, by the energy which was stored during setting of the dose in the drive spring 61. The rotation of the drive member 21 causes the piston rod 22 to rotate relative to the nut member 31 and hence the piston rod 22 moves axially with respect to the nut member 31 due to the threaded interaction of the piston rod 22 with the nut member 31 (cf. piston rod thread 29 and nut member thread 35 in FIG. 2A). This causes the piston 73 to be advanced in the cartridge 19 which in turn may be retained in the cartridge holder 11 (cf. FIG. 1). Thereby, the drug 80 or medicament may be dispensed from the cartridge 19. During the relative rotational movement of the drive member 21 in the counter clockwise direction with respect to the nut carrier 32, the clicker arms 44 ride over the drive clutch splines 47, thereby producing an audible feedback as the clicker arms 44 snap back or relax into their original position. The rotation of the dial member 23 with respect to the housing assembly 10 causes the display member 27 to rotate towards the inner housing stop 58, thereby reducing the number of unit s displayed to the user through the window 16. Drug will continue to be delivered until the display member end stop face 53 abuts the inner housing stop 58, thus preventing any further rotation of the drive assembly 20 (cf. FIG. 17C). The operation of dispensing a dose can be interrupted by releasing the trigger member 71. When the trigger member 71 is released, the clutch mechanism between the drive member 21 and the nut carrier 32 is reengaged such that the drive member 21 is again rotationally locked with respect to the nut carrier 32. This reengagement occurs, as the clutch spring 41 tends to urge the drive member 21 and the nut carrier 32 away from each other such that the drive clutch splines 47 and the carrier clutch splines 48 are reengaged. Thereby, the drug delivery device returns to the setting mode of operation. Then, either the rest of the dose may be dispensed or another dose may be chosen by the user.

The term "drug" or "medicament" as used herein may mean a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39), des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Trp(O2)25, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The scope of protection is not limited to the examples given herein above. The invention is embodied in each novel characteristic and each combination of characteristics, which particularly includes every combination of any features which are stated in the claims, even if this feature or this combination of features is not explicitly stated in the claims or in the examples.

REFERENCE NUMERALS

1 Drive mechanism
2 Ramp (clockwise)
3 Ramp (counter clockwise)
4 Interaction surface
10 Housing assembly
11 Cartridge holder
12 Insert
13 Insert connection element
14 Body
15 Inner housing
16 Window
17 Cartridge connection element
18 Retention face
19 Cartridge
20 Drive assembly
21 Drive member
22 Piston rod
23 Dial member
24 Dial member spline
25 Piston rod spline
26 Drive member spline
27 Display member
28 Display member thread
29 Piston rod thread
30 Nut assembly
31 Nut member
32 Nut carrier
33 Nut carrier thread
34 Nut member spline
35 Nut member thread
36 Nut carrier ratchet teeth
37 Nut carrier recess
38 Carrier connection element
39 Dispense clicker
41 Clutch spring
42 Drive member abutment face
43 Nut carrier abutment face
44 Clicker arm
45 Drive clutch feature
46 Carrier Clutch feature
47 Drive clutch spline
48 Carrier clutch spline
49 Drive assembly connection element
50 Proximal opening
51 Inner housing connection element
52 Collar
53 Display member end stop face
55 Body stop
56 Display member maximum stop face
57 Inner housing thread
58 Inner housing stop
59 Indicia
61 Drive spring
62 Distal termination
63 Proximal termination
64 Drive member recess
65 Inner housing recess
66 Dose nut splines
67 Dose nut stop feature
71 Trigger member
72 Bearing
73 Piston
74 Insert ratchet teeth
75 Housing connection element
76 Proximal end
77 Distal end
78 Distal face
79 Proximal face
80 Drug
81 Dose nut
82 Distal nut member abutment face
83 Nut carrier stop face
84 Proximal nut member abutment face 85 Distal trigger member face
86 Protrusion
87, 88, 89 Arrows
100 Drug delivery device
X Longitudinal axis

The invention claimed is:

1. A drive mechanism for use in a drug delivery device, the drive mechanism comprising:
   a housing having a proximal end and a distal end,
   a piston rod which is rotatable with respect to the housing, wherein the piston rod is configured to drive a piston toward the distal end of the housing, and
   a nut member which mechanically cooperates with the piston rod and which is selectively rotationally lockable with respect to the housing,
   wherein the drive mechanism is switchable between a setting mode of operation and a dispensing mode of operation, the drive mechanism being configured such that:
      in the setting mode of operation in which a dose can be set, the nut member and the piston rod are rotatable with respect to the housing in a first direction and in a second direction opposite to the first direction, and
      in the dispensing mode of operation, the piston rod is rotatable with respect to the housing and the nut member is rotationally locked with respect to the housing, wherein, when the piston rod rotates, the piston rod moves distally with respect to the nut member.

2. The drive mechanism according to claim 1, wherein the nut member is axially locked with respect to the housing.

3. The drive mechanism according to claim 1, wherein the nut member is part of a nut assembly further comprising a nut carrier which is rotationally locked to the nut member, and
   wherein the drive mechanism comprises a selective rotational locking connection which is configured such that:
      in the setting mode of operation, the selective rotational locking connection is released and the nut carrier is rotatable with respect to the housing, and
      in the dispensing mode of operation, the selective rotational locking connection is established, thereby rotationally locking the nut carrier with respect to the housing.

4. The drive mechanism according to claim 3, wherein the housing comprises a housing connection element and the nut carrier comprises a carrier connection element, wherein the housing connection element and the carrier connection element are configured to cooperate in order to establish the selective rotational locking connection.

5. The drive mechanism according to claim 4, wherein the selective rotational locking connection is configured to produce audible and/or tactile feedback when the nut carrier is rotated with respect to the housing in the setting mode of operation.

6. The drive mechanism according to claim 1, wherein the drive mechanism comprises a drive member, which mechanically cooperates with the piston rod, wherein the drive member is configured to drive movement of the piston rod in the dispensing mode of operation, wherein the drive mechanism comprises a clutch mechanism operable to releasably rotationally lock the drive member with respect to the nut member, and wherein, in the setting mode of operation, the drive member is rotationally locked with respect to the nut member, and in the dispensing mode of operation, the drive member is rotatable with respect to the nut member.

7. The drive mechanism according to claim 6, wherein:
   the nut member is part of a nut assembly further comprising a nut carrier which is rotationally locked to the nut member and wherein the drive mechanism comprises a selective rotational locking connection which is configured such that:
      in the setting mode of operation, the selective rotational locking connection is released and the nut carrier is rotatable with respect to the housing, and
      in the dispensing mode of operation, the selective rotational locking connection is established, thereby rotationally locking the nut carrier with respect to the housing, and
   the drive member comprises a drive clutch feature and the nut carrier comprises a carrier clutch feature, wherein the drive clutch feature and the carrier clutch feature are part of the clutch mechanism and configured such that:
      when the drive mechanism is in the setting mode of operation, the drive clutch feature and the carrier clutch feature are engaged, and
      when the drive mechanism is in the dispensing mode of operation, the drive clutch feature and the carrier clutch feature are disengaged.

8. The drive mechanism according to claim 1, wherein the drive mechanism comprises a trigger member which is operable to switch the drive mechanism from the setting mode of operation to the dispensing mode of operation.

9. The drive mechanism according to claim 8, wherein:
   the drive mechanism comprises a drive member, which mechanically cooperates with the piston rod, wherein the drive member is configured to drive movement of the piston rod in the dispensing mode of operation, wherein the drive mechanism comprises a clutch mechanism operable to releasably rotationally lock the drive member with respect to the nut member, and wherein, in the setting mode of operation, the drive member is rotationally locked with respect to the nut member, and in the dispensing mode of operation, the drive member is rotatable with respect to the nut member, and
   the clutch mechanism is configured such that, when the drive mechanism is in the setting mode of operation and the trigger member is operated, the drive member is moved distally with respect to the nut member, thereby disengaging a drive clutch feature of the drive member and a carrier clutch feature of the nut member in order to switch the drive mechanism from the setting mode of operation into the dispensing mode of operation.

10. The drive mechanism according to claim 1, wherein the drive mechanism comprises a dial member which is configured to be rotated by a user with respect to the housing in the setting mode of operation to set a dose, the dial member being rotationally locked to the piston rod.

11. The drive mechanism according to claim 10, wherein the drive mechanism is configured such that, in the setting mode of operation, the nut member and the piston rod are rotatable in the first direction with respect to the housing, when a dose is set, and wherein the nut member and the piston rod are rotatable in the second direction, opposite to the first direction with respect to the housing, when the set dose is cancelled.

12. The drive mechanism according to claim 10, wherein:
the nut member is part of a nut assembly further comprising a nut carrier which is rotationally locked to the nut member and wherein the drive mechanism comprises a selective rotational locking connection which is configured such that, in the setting mode of operation, the selective rotational locking connection is released and the nut carrier is rotatable with respect to the housing, and wherein, in the dispensing mode of operation, the selective rotational locking connection is established, thereby rotationally locking the nut carrier with respect to the housing, the drive member comprises a drive clutch feature and the nut carrier comprises a carrier clutch feature, wherein the drive clutch feature and the carrier clutch feature are part of a clutch mechanism and configured such that:
when the drive mechanism is in the setting mode of operation, the drive clutch feature and the carrier clutch feature are engaged, and
when the drive mechanism is in the dispensing mode of operation, the drive clutch feature and the carrier clutch feature are disengaged, and the drive mechanism comprises a drive spring which is mechanically coupled to the drive member and to the housing, wherein the drive spring is arranged and configured such that the drive spring is biased when the dial member is operated to set a dose in the setting mode of operation, whereby energy is stored in the drive spring, and the drive spring is released in the dispensing mode of operation such that the stored energy is used to drive movement of the drive member.

13. The drive mechanism according to claim 3, wherein the drive mechanism comprises a dose nut which mechanically cooperates with the nut carrier, wherein the nut carrier and the dose nut are arranged and configured such that, when the drive mechanism is in the setting mode of operation, the nut carrier is rotatable with respect to the dose nut such that a rotation of the nut carrier is converted into an axial movement of the dose nut with respect to the nut carrier.

14. The drive mechanism according to claim 7, wherein the nut carrier comprises a dispense clicker which is arranged and configured to interact with the drive clutch feature of the drive member when the drive mechanism is in the dispensing mode of operation, whereby an audible and/or tactile feedback is provided.

15. A drug delivery device comprising:
a drive mechanism comprising: a housing having a proximal and a distal end, a piston rod which is rotatable with respect to the housing, wherein the piston rod is configured to drive a piston toward the distal end of the housing, and a nut member which mechanically cooperates with the piston rod and which is selectively rotationally lockable with respect to the housing, wherein the drive mechanism is switchable between a setting mode of operation and a dispensing mode of operation, the drive mechanism being configured such that:
in the setting mode of operation in which a dose can be set, the nut member and the piston rod are rotatable with respect to the housing in a first direction and in a second direction opposite to the first direction, and
in the dispensing mode of operation, the piston rod is rotatable with respect to the housing and the nut member is rotationally locked with respect to the housing, wherein, when the piston rod rotates, the piston rod moves distally with respect to the nut member,
wherein the drug delivery device is a pen- and/or an injector-type device.

16. A drug delivery device comprising the drive mechanism according to claim 1, wherein the drug delivery device is a pen-type device and/or an injector-type device.

* * * * *